(12) United States Patent
Bonrath et al.

(10) Patent No.: US 7,626,046 B2
(45) Date of Patent: Dec. 1, 2009

(54) MANUFACTURE OF α-TOCOPHEROL

(75) Inventors: Werner Bonrath, Freiburg (DE); David Carl Burdick, Peoria, IL (US); Frank Schager, Loerrach (DE); Dominik Thomas, Munich (DE); Thomas Netscher, Bad Krozingen (DE)

(73) Assignee: DSM IP Assets B.V., TE Heerlen (NL)

( * ) Notice: Subject to any disclaimer, the term of this patent is extended or adjusted under 35 U.S.C. 154(b) by 458 days.

(21) Appl. No.: 10/494,005

(22) PCT Filed: Oct. 23, 2002
(Under 37 CFR 1.47)

(86) PCT No.: PCT/EP02/11819

§ 371 (c)(1),
(2), (4) Date: Apr. 26, 2005

(87) PCT Pub. No.: WO03/037883

PCT Pub. Date: May 8, 2003

(65) Prior Publication Data
US 2005/0187393 A1    Aug. 25, 2005

(30) Foreign Application Priority Data
Oct. 31, 2001    (EP)    ................. 01125966

(51) Int. Cl.
*C07D 311/72*    (2006.01)
(52) U.S. Cl. ...................................... 549/408
(58) Field of Classification Search ............ 549/408
See application file for complete search history.

(56) References Cited

U.S. PATENT DOCUMENTS 4,208,334 A    6/1980    Fitton et al.

FOREIGN PATENT DOCUMENTS

EP    1 134 218 A1    9/2001

OTHER PUBLICATIONS

Cohen et al., J. Org. Chem. (1981), vol. 46(12), p. 2445-2450.*
Meyer et al., Helv. Chim. Acta, (1967), vol. 50(120), pp. 1168-1178.*
Stocker, A. et al., "Identification of the Tocopherol-Cyclase in the Blue-Green Algae *Anabaena variabilis* Kützing (Cyanobacteria)", *Helvetica Chimica Acta*, vol. 76, pp. 1729-1738 (1993).
Bulychev, É. and Shchegolev, A., "Some Technological Features of Using Heterogeneous Catalysis in the Synthesis of α-Tocopherol", *Pharmaceutical Chemistry Journal*, vol. 33(2), pp. 98-100 (1999). Translated from *Khimiko-Farmatsevticheskii Zhurnal*, vol. 33(2), pp. 40-42 (1999).
Wang, S. et al., "The Synthesis of D L - α-tocopherol in Supercritical Media", *Journal of Supercritical Fluids*, vol. 17, pp. 135-143 (2000).
Shchegolev, A. et al., "Synthesis of Vitamin E Acetate", *M.V. Lomonosov Institute of Precision Chemical Engineering, Moscow*, pp. 71-73 (1983) Translated from *Khimiko-Farmatsevticheskii Zhurnal*, vol. 17(1), pp. 92-95 (1983) .
Matsui, et al. "Synthesis of a-tocopherol: scandium(III) trifluoromethanesulfonate as an efficient catalyst in the reaction of . . . " Bull. Chem. Soc. Jpn., 68, 3569-3571 (1995).
Baldwin, J.E., et al. "5-Endo-Trigonal Reactions: a Disfavoured Ring Closure," J. Chem. Soc., Chem. Commun., 736 (1976).
Baldwin, J.E., "Rules for Ring Closure," J. Chem. Soc., Chem. Commun., 734-736 (1976).

* cited by examiner

*Primary Examiner*—Taofiq A Solola
(74) *Attorney, Agent, or Firm*—Bryan Cave LLP

(57) ABSTRACT

A process for the manufacture of (all-rac)-α-tocopherol comprises submitting isolated, purified phytyltrimethylhydroquinone to acid catalysis, thereby promoting ring closure to (all-rac)-α-t-tocopherol. The process can be conducted in the absence or presence of an added solvent, and when a solvent or solvent mixture is used the solvent or at least one solvent component of the solvent mixture is preferably one with a dipole moment greater than $9 \times 10^{-30}$ C-m (or 2.7D). The nature of the catalyst is immaterial, but the catalyst is preferably sulphuric acid, phosphoric acid, a polyperfluoroalkylenesulphonic acid, a "NH-acid", a heteropoly acid, zinc chloride, boron trifluoride, aluminium trichloride, or a mixture of any f the aforementioned Brönsted acids with any of the aforementioned Lewis acids. The product of the process is the most active an industrially most important member of the vitamin E group.

44 Claims, 1 Drawing Sheet

MANUFACTURE OF α-TOCOPHEROL

This application is the National Stage of International Application No. PCT/EP02/11819, filed Oct. 23, 2002.

The present invention concerns a process for the manufacture of (all-rac)-α-tocopherol by the acid-catalyzed cyclization (or "ring closure") of phytyltrimethyl-hydroquinone. As is known, (all-rac)-α-tocopherol (or as it has mostly been denoted in the prior art, "dl-α-tocopherol"), is a diastereomeric mixture of 2,5,7,8-tetramethyl-2-(4', 8', 12'-trimethyltridecyl)-6-chromanol (α-tocopherol), which is the most active and industrially most important member of the vitamin E group.

(all-rac)-α-Tocopherol is generally manufactured industrially by the acid-catalyzed reaction of trimethylhydroquinone (TMHQ) with isophytol (IP), which is believed to involve essentially two chemical steps, i.e. the alkylation of TMHQ with isophytol, leading in particular to phytyltrimethylhydroquinone (PTMHQ), followed by the ring closure of the PTMHQ to (all-rac)-α-tocopherol. The two chemical steps are effected in the same medium of solvent or mixed solvents and catalyst, and under the same reaction conditions, e.g. in an optimized narrow temperature range. Moreover, the one reactant, normally the IP, is usually employed in an excess amount over the amount of the other reactant, and no attempt is made to isolate and optionally purify the intermediate produced in the first chemical step, i.e. the alkylation step, PTMHQ, before submitting this intermediate to the ring closure step leading to the final product, (all-rac)-α-tocopherol. In all cases the procedure must be carefully optimized to obtain maximum selectivity and yield of (all-rac)-α-tocopherol within typical industrial manufacturing constraints of productivity and cost. Most of these procedures furnish the tocopherol in a crude state which is highly coloured and often not more than 90% pure, which then requires additional purification operations in order to achieve the high purity required for food and pharmaceutical use. The above-described situation is reflected in the scientific and patent literature, in which a large number of acid catalysts, solvents and reaction conditions, e.g. temperatures, are disclosed for the manufacture of (all-rac)-α-tocopherol from TMHQ and IP by the essentially "one-pot" or "through process" methodology.

Figure 1:
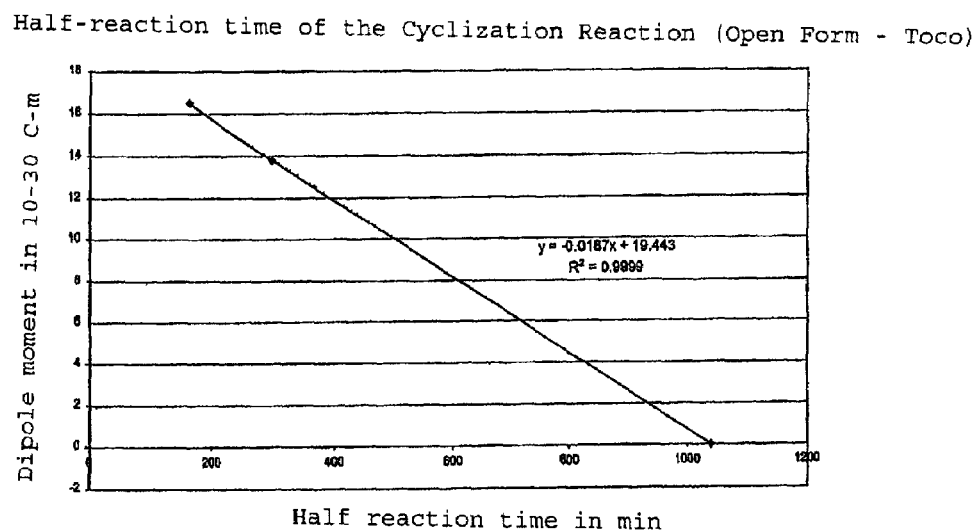
FIG. 1 shows a graph of half-reaction time of the cyclization reaction.

It has been assumed that the reaction of TMHQ with IP gives transient intermediates, particularly PTMHQ, which are either not normally observed, or occur in small amounts, at intermediate stages of the process [see for example, Schegovev et al., Khimiko-farmatsevticheskii Zhurnal 17, 1, 93-95 (1983) and Wang et al., J. Supercritical Fluids 17, 135-143 (2000)]. By using less vigorous reaction conditions, the intermediate PTMHQ can be accumulated to some degree, then isolated by chromatography and minimally characterized [Schegovev et al, loc cit, and Khimiko-farmatsevticheskii Zhurnal 33, 40-42 (1999)]. PTMHQ has been shown to be convertible to α-tocopherol when subjected to more typically vigorous acidic reaction conditions. In these publications nothing is stated about the selectivity or yield of the reaction. Others have shown that the homochiral analogue of PTMHQ is converted to RRR-α-tocopherol through the action of tocopherol cyclase enyzmes [Woggon et al., Bioorg. Med. Chem. 4, 1129-34 (1986) and Helv. Chim. Acta 76, 1729 (1993)]. In this work, both the conversion and the yield are reported to be high, but the conditions used for the transformation are significantly different from those employed for the chemical transformations. Thus the by-products and selectivity of the chemical transformation are hitherto unknown.

(all-rac)-α-Tocopherol as normally produced in crude form by the reaction of TMHQ with IP is well known to persons engaged in the technical field to be highly coloured and to contain various by-products, such as phytadienes and their polymers, diastereomers of substituted benzofuran isomers of tocopherol, and other known and as yet unidentified by-products in amounts which vary from a few percent to 10% or more. The genesis of these products is not known with certainty. These by-products must be removed from the crude (all-rac)-α-tocopherol or its acetate by various means, such as distillation, in order to obtain highly pure (all-rac)-α-tocopherol acetate. This results in additional operating and capital expenses. Furthermore, the purification methods are not usually sufficiently efficient, so that small amounts of these by-products are unavoidably present in the commercial product.

In the scope of the present invention is has now been found that PTMHQ in isolated, purified form and fully characterized as such can surprisingly be converted to (all-rac)-α-tocopherol in very high yield, in some cases in nearly quantitative yield, and with almost complete selectivity. Thus it is possible for the first time to obtain (all-rac)-α-tocopherol from reaction mixtures in a form which does not require further extensive purification, since it is virtually free of by-products which otherwise occur, i.e. when the "through process" methodology is employed.

Moreover, it has been found that this pertinent ring closure reaction occurs cleanly using various acid catalysts and solvents which when used in the "through process" do not enable equivalent high selectivities and yields. The ring closure proceeds particularly efficiently in solvents with a high dipole moment.

In particular, it has been surprisingly found that the efficiency of the ring closure is dramatically enhanced if isolated, purified PTMHQ is used as the starting material instead of its precursors TMHQ and IP. Moreover, the employed solvent is preferably one which has a high dipole moment, particularly one greater than $9 \times 10^{-30}$ Coulomb-metre (C-m). Expressed using an alternative unit, the dipole moment of the employed solvent is greater than 2.7 Debye (D).

Accordingly, the object of the present invention is to provide a process for the manufacture of (all-rac)-α-tocopherol selectively and in high yield, thus avoiding the production of undesired by-products. This object is achieved by using isolated, purified PTMHQ as the starting material. The solvent, the acid catalyst and the further reaction conditions under which the reaction is performed, e.g. the reaction temperature, may correspond essentially to those used hitherto for the process of manufacturing (all-rac)-α-tocopherol from TMHQ and IP. However, in respect of the solvent, this is preferably one with a high dipole moment, particularly one greater than $9 \times 10^{-30}$ C-m (or 2.7 D). Thus, in accordance with the process of the present invention, there is provided a process for the manufacture of (all-rac)-α-tocopherol, characterized by submitting isolated, purified phytyltrimethylhydroquinone to acid catalysis, thereby promoting ring closure to (all-rac)-α-tocopherol. The solvent or at least one component of a solvent mixture in which the ring closure reaction is performed is preferably one with a high dipole moment, particularly a dipole moment greater than $9 \times 10^{-30}$ C-m (or 2.7 D).

The ring closure reaction involved is represented in the following Reaction Scheme:

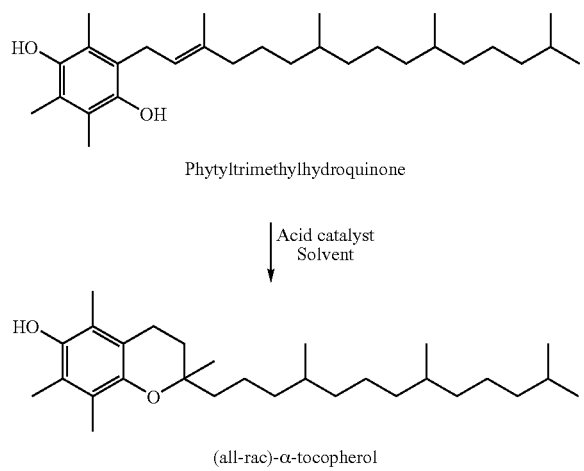

Phytyltrimethylhydroquinone

↓ Acid catalyst
  Solvent (all-rac)-α-tocopherol

The PTMHQ used as the starting material of the process of the present invention may be produced by any desired known or as yet unknown means. For example, it is known from the teachings of U.S. Pat. No. 4,208,334 (Fitton et al.) that the reaction of TMHQ with IP may be carried out in a combined solvent and catalyst medium of the Brönsted acid trifluoroacetic acid or its anhydride. In contrast thereto it has been found that on employing merely catalytic amounts of trifluoroacetic acid or its anhydride and an added solvent, particularly a two-phase solvent system such as ethylene carbonate and heptane or propylene carbonate and heptane, PTMHQ is predominantly formed rather than (all-rac)-α-tocopherol, whereby the reaction is effected generally at temperatures from about 20° C. to about 140° C., particularly those in the range from about 40° C. to about 120° C., and most preferably in the range from about 80° C. to about 100° C. Under such conditions the desired alkylation of TMHQ with IP occurs, but not the subsequent ring closure step to any appreciable extent. In other respects, including in general the choice of solvent in which the reaction is performed, the conditions given in said US patent specification may be utilized. Accordingly, there may be used as the solvent in the reaction to produce PTMHQ a more conventional solvent such as toluene, heptane, methylene chloride, acetic acid, diethyl ether or an aromatic hydrocarbon, e.g. benzene or an xylene, with less amount, i.e. a catalytic amount, of catalyst. As indicated above, a mixed (two-phase) ethylene or propylene carbonate—heptane system is preferably employed as the solvent; in this case the volume ratio of ethylene or propylene carbonate to heptane (the latter as 1 unit of volume) is conveniently in the range from about 0.8:1 to about 1.25:1.

Other known methods may be used to produce the required starting material PTMHQ, and indeed the process of the present invention is by no means limited to the actual process for obtaining the starting PTMHQ.

Regardless of the method of production of the starting material, PTMHQ, the "isolated, purified phytyltrimethylhydroquinone" employed in the process of the present invention is pure to the extent of at least 95%. In general, the purer the PTMHQ, the more preferred it is for use as the starting material. A purity of at least 98% for the starting material PTMHQ is preferred. In any event the PTMHQ may be isomerically pure E or Z isomer, or it may be a mixture of E and Z isomers in any desired or obtained proportion. Should a less pure PTMHQ product be obtained, i.e. one with a determined purity of less than 95%, then such product can be purified to the extent required for the process by methods of purification known to those skilled in the art, such as crystallization, liquid-liquid extraction, supercritical fluid extraction, simulated moving bed chromatography or distillation. The subsequent ring closure reaction is surprisingly very clean and selective, and so the degree of purity of the PTMHQ exerts a decisive influence on the yield and the purity in which the (all-rac)-α-tocopherol is produced from the PTMHQ in the process of the present invention.

The conversion of PTMHQ to (all-rac)-α-tocopherol is effected in principle by subjecting the PTMHQ, in liquid form (the PTMHQ being used as such without any added solvent) or in solution, to the action of an acid catalyst at suitable temperatures. After removal of the catalyst, substantially pure crude (all-rac)-α-tocopherol may be isolated free of any solvent used or, if desired, converted in situ to (all-rac)-α-tocopherol acetate.

The choice of solvents includes any solvent (including a solvent mixture), which clearly has to meet the criteria of not destructively interacting with the PTMHQ, the produced (all-rac)-α-tocopherol or the acid catalyst, of at least partially dissolving the PTMHQ under the reaction conditions, and of being capable of remaining in the liquid state at the reaction temperatures with or without requiring the application of elevated pressure to maintain said state. Moreover, the selected solvent or at least one solvent of a solvent mixture (particularly a two-phase solvent system) preferably has a dipole moment greater than $9 \times 10^{-30}$ C-m (or 2.7 D). In general the solvent may be a liquid at room temperature and normal pressure, a liquid at elevated pressure, a liquefied gas (e.g. a gas in a supercritical state, i.e. a so-called supercritical fluid), or a two- or multiphase solvent system such as an emulsion or a micelle. As indicated above, PTMHQ itself may be reacted without the addition of a solvent, and in this case it is generally in liquid, e.g. paste-like, form. Preferably, there is used as the solvent satisfying the above criteria a single polar solvent or a solvent mixture in which at least one polar solvent is present.

Examples of classes of solvents, with in each case one or more specific members thereof (their respective dipole moments being given in parenthesis), in the above-mentioned categories are as follows:

Liquids at Room Temperature and Normal Pressure:

Aliphatic and aromatic hydrocarbons, e.g. heptane (zero), toluene (1.0 D) and nitrobenzene (13.3 D);

Halogenated (particularly chlorinated) aliphatic and aromatic hydrocarbons, e.g. methylene chloride (5.2 D), 1,2-dichloroethane (6.1 D) and chlorobenzene (5.4 D);

Aliphatic and cyclic ethers, e.g. dibutyl ether (3.9 D), dimethoxyethane (5.7 D), tetrahydrofuran (5.8 D) and dioxan (1.5 D);

Aliphatic, cyclic and aromatic esters, e.g. ethyl acetate (6.1 D), diethyl carbonate (3.0 D), propylene carbonate (16.5 D) and γ-butyrolactone (13.7 D);

Aliphatic and aromatic, and mixed aliphatic/aromatic, ketones, e.g. 2-butanone (9.2 D) and 4-methyl-2-pentanone (2.7 D);

Amides, e.g. dimethylformamide (10.8 D) and N-methylpyrrolidone (13.6 D);

Sulphones, e.g. sulpholane (16.0 D);

Liquids at Elevated Pressure:

The above hydrocarbons, ethers, esters, ketones, amides and sulphones used at temperatures above their normal boiling points and maintained in liquid form by the application of elevated pressures, especially the solvents butane and methylene chloride, and also carbon disulphide under such conditions;

Liquefied Gases:

Propane, carbon dioxide, sulphur dioxide and nitrous oxide under appropriate elevated pressure;

Two- or Multiphase Systems:

An aliphatic hydrocarbon with an aliphatic, cyclic or aromatic ester, e.g. heptane and ethylene carbonate or propylene carbonate.

Some of the above classes of solvents and specific members thereof feature a dipole moment greater than $9 \times 10^{-30}$ C-m (or 2.7 D), and these are preferred for use in the process of the present invention. The permanent dipole moment of any such solvent can be measured by methods known in the literature concerning physical organic chemistry, e.g. C. Reichardt, Solvents and Solvent Effects in Organic Chemistry (VCH, 1990) and Y. Marcus, The Properties of Solvents (Wiley, 1999). Other preferred classes of solvents are those classes of solvents listed above under the category "liquids at room temperature and normal pressure" other than aliphatic and aromatic hydrocarbons, halogenated (particularly chlorinated) aliphatic hydrocarbons and aliphatic esters.

The process according to the present invention is effected under acid catalysis, i.e. in the presence of an acid catalyst. In principle, any Brönsted or Lewis acid, or a mixture of both types, may be used, and the scientific and patent literature pertaining to the manufacture of α-tocopherol from TMHQ and IP (or phytol or a derivative thereof) discloses many such catalysts for this purpose. Amongst the suitable Brönsted acid catalysts may be mentioned, for example, sulphuric acid; phosphoric acid; such "super acids" as the polyperfluoroalkylenesulphonic acids available under the trademark Nafion®; such "NH-acid" compounds as bis(trifluoromethanesulphonyl)amine, $(CF_3SO)_2NH$; and such heteropoly acids as 12-tungstophosphoric acid. Amongst the suitable Lewis acid catalysts may be mentioned, for example, zinc chloride, boron trifluoride and aluminium trichloride. These and further such suitable catalysts are disclosed in the prior art, for example in such European Patent Publications (EP) as EP 782,993, EP 784,042, EP 937,055, EP 949,255, EP 970,953, EP 1,000, 940 and EP 1,134, 218, or described in the as yet unpublished European Patent Applications 0119322.4, 01101026.1 and 01122499.5.

Preferably the catalyst is a Brönsted acid (protic acid) or mixture of two or more such acids, e.g. sulphuric acid, p-toluenesulphonic acid, Nafion® NR 50, 12-tungsto-phosphoric acid or bis(trifluoromethanesulphonyl)amine, in particular a Brönsted acid or mixture of two or more Brönsted acids, such as one of more of these exemplified ones, in the absence of any further types of acid catalysts.

The process is conveniently effected at temperatures from about −20° C. to about +200° C., preferably from about 0° C. to about 150° C., and most preferably from about 90° C. to about 130° C.

Conveniently the amount of solvent used, expressed in terms of the weight percent (wt.%) of the starting material PTMHQ relative to the weight of solvent is such that the wt.% of PTMHQ varies from about 0.1 to about 100 wt. %, this range including cases where the PTMHQ is not completely dissolved in the solvent. At the very upper part of this range the PTMHQ is understood to be used without the addition of a solvent ("100% wt. %" means that 100% pure PTMHQ is subjected to the acid-catalysed ring closure reaction in the complete absence of a solvent). Preferably, however, the wt.% of PTMHQ in the (added) solvent is from about 2 to about 20 wt. %.

The suitable amount of any given catalyst used must be determined empirically, taking due account of the particular catalyst involved and the other variable reaction parameters. Pertinent information is provided in the literature, particularly patent literature, concerning the manufacture of α-tocopherol from TMHQ and IP or phytol (derivatives), as given hereinbefore. In the present case the basis is of course the amount of PTMHQ employed, and the relative amount of catalyst thereto is generally from about 0.001 to about 20 wt. %, preferably from about 0.1 to about 10 wt. %.

As is usual in the manufacture of α-tocopherol, the process of the present invention is conveniently carried out under an inert gas atmosphere, preferably gaseous nitrogen or argon.

The actual reaction generally lasts for about 1 to about 30 hours, preferably about 2 to about 24 hours, especially about 3 to about 18 hours.

Generally the reaction is conducted in the usual manner known to skilled chemists and engineers by subjecting PTMHQ to the action of the acid catalyst(s) with suitable mixing in fluid phase until the conversion is complete or substantially complete. Known engineering options such as standard stirred autoclaves, cascade reactors, loop reactors, fixed catalyst beds, etc. which allow efficient practice may be employed. The catalyst may be removed by conventional means, such as filtration, extraction, adsorption, etc. The solvent too may be removed by conventional means, such as distillation, to furnish pure (all-rac)-α-tocopherol. Alternatively, the reaction mixture, with or without removal of catalyst, may be directly treated with acetylation agents such as acetic anhydride, acetic acid or an acetic ester to convert the free tocopherol to (all-rac)-α-tocopherol acetate.

The process in accordance with the invention is illustrated by the following Examples:

EXAMPLE 1

Preparation of Starting Material Phytyltrimethylhydroquinone

A mixture of trimethylhydroquinone (15.5 g, 100 mmol), propylene carbonate (100 ml) and heptane (100 ml) was heated to 140° C. (bath temperature) in a three-necked reaction flask equipped with a water separator, a reflux condenser and argon gasification means. Trifluoroacetic acid (0.5 ml, 6.52 mmol) was then added dropwise using a syringe to the biphasic reaction mixture at reflux temperature, followed by isophytol (35.99 ml, 100 mmol) to the resulting solution over a period of 30 minutes at 140° C. (internal temperature 100° C.). After stirring for a further 10 minutes at 140° C., water and heptane were distilled off from the reaction mixture. The produced phytyltrimethylhydroquinone was extracted with three 50 ml portions of heptane from the carbonate phase, and the combined heptane phase was cooled down to room temperature. The resulting yellowish suspension was filtered through a P4 frit (requiring 2-3 days) and washed with 100 ml of cold propylene carbonate (4° C.) and 500 ml of cold heptane (4° C.) to remove traces of trimethylhydroquinone and by-products. The white waxy residue was dried for 3 hours under high vacuum. The so produced phytyltrimethylhydroquinone was found to have a purity of about 95%.

$^1$H-NMR (CDCl$_3$, 400.4 MHz): δ=0.85-0.95 (m, 12H, 4 CH$_3$), 0.97-1.57 (m, about 19 aliph. H), 1.60-1.64 and 1.67-1.71 (2×m, 1 arom. CH$_3$, Z and E), 1.88-2.22 (m, 11 H, 5 aliph. H+2 arom. CH$_3$), 3.30 (d, CH$_2$—CH=C, J=6.7 Hz, E), 3.34 ("d", CH—CH=C, J=6.7 Hz, Z), 3.71 and 3.72 (2×s, OH, E and Z), 4.39 and 4.40 (2×s, OH, E and Z), 5.14 and 5.17 ppm (2×"t", CH=C, J=about 6.6 and 6.8 Hz, Z and E); E:Z=70:30;

IR (film, cm$^{-1}$): 3350s, 2925s, 1460s, 1380w, 1335m, 1245s, 1175m, 1085s, 1055m, 945w, 840m;

MS (EI): m/e=430 (76%, M$^+$), 205 (19, [M-C$_{16}$H$_{33}$]$^+$), 165 (100, C$_{10}$H$_{13}$O$_2^+$), 164 (98);

Elemental analysis: C$_{29}$H$_{50}$O$_2$ (430.717): Calc. C 80.87%, H 11.70%; Found C 80.75%, H 11.77%.

The product, phytyltrimethylhydroquinone, was also characterized as its diacetate, a colourless paste, with the following results:

$^1$H-NMR (CDCl$_3$, 250.1 MHz): δ=0.80-0.92 (m, 12H, 4 CH$_3$), 0.94-1.60 (m, about 19 aliph. H), 1.65 and 1.71 (2×m$_c$, 1 arom. CH$_3$, Z and E), 1.86-2.18 (m, 11H, 5 aliph. H+2 arom. CH$_3$), 2.31 (s, Ac—CH$_3$), 2.34 (s, Ac—CH$_3$), 3.20 (m$_c$, CH$_2$—CH=C), 4.95 ppm ("t", CH=C, J=about 6 Hz). E:Z=70:30;

IR (film, cm$^{-1}$): 2953s, 1783s, 1462s, 1367s, 1195s, 1080m, 1053w, 1010w, 909w, 888w, 840w;

MS (EI): m/e=514 (7%, M$^+$), 471 (37, [M-COCH$_3$]$^+$), 430 (100, [M-2 COCH$_2$]$^+$), 207 (34), 165 (52, C$_{10}$H$_{13}$O$_2^+$), 164 (38);

Elemental analysis: C$_{33}$H$_{54}$O$_4$ (514.791): Calc. C 77.00%, H 10.57%; Found C 77.44%, H 10.48%.

The phytyltrimethylhydroquinone was further purified by washing with methanol at −20° C. Said washing was effected on a P4 frit (300 ml for 20 g of the product), and the analysis of the obtained purer material was effected by gas chromatography (GC). A purity of 97.1% (area %) was established. The results of the purification method are presented in the following table:

TABLE 1

Purification of phytyltrimethylhydroquinone

| Composition of purified product | Amount of constituent relative to whole product |
| --- | --- |
| TMHQ | 0.5 |
| Phytadienes | 0.3 |
| (all-rac)-α-Tocopherol | 0.2 |
| Phytyltrimethylhydroquinone | 97.1 |
| Yield (based on crude phytyltrimethylhydroquinone) | <50% |

EXAMPLE 2

Ring Closure of Purified Phytyltrimethylhydroquinone: Determination of Selectivity 1.03 g (2.39 mmol) of purified phytyltrimethylhydroquinone were transferred to a Schlenk tube and dissolved in a mixture of propylene carbonate (10 ml; dipole moment 16.5 D) and heptane (10 ml; zero dipole moment). The reaction mixture was heated to 100° C. (internal temperature), and the ring closure was initiated by adding the catalyst solution (10 mol % of catalyst). During one hour at a bath temperature of 140° C. the internal temperature increased to 120-125° C. by distilling off heptane. The reaction mixture was then cooled down to room temperature, and the separated carbonate phase was extracted three times with heptane. The combined heptane phases were evaporated, and the colourless residue analyzed by GC, the results thereof being presented in the following table:

TABLE 2

Selectivity of the ring closure reaction

| Starting material: | | |
| --- | --- | --- |
| Purity: | 97.7% E/Z phytyltrimethylhydroquinone | |
| Impurities | 0.4% TMHQ, 0.3% phytadienes, 0.2% (all-rac)-α-tocopherol | |
| Using a heteropoly acid as the catalyst: | | |
| Selectivity | 99.9% | |
| Impurities | phytyltrimethylhydroquinone | 0.15% |
| | phytadienes | 0.3% |
| Using sulphuric acid as the catalyst: | | |
| Selectivity | 99.9% | |
| Impurities | phytyltrimethylhydroquinone | 0.1% |
| | phytadienes | 0.3% |
| Using p-toluenesulphonic acid as the catalyst: | | |
| Selectivity | 99.9% | |
| Impurities | phytyltrimethylhydroquinone | 0.2% |
| | phytadienes | 0.9% |

EXAMPLE 3

Cyclization of Phytyltrimethylhydroquinone to (all-rac)-α-tocopherol with Various Catalysts A stock solution of the phytyltrimethylhydroquinone (23.76 g, 63.5 mmol) in distilled propylene carbonate (543 ml; dipole moment 16.5 D) was prepared under an argon atmosphere.

20 ml of stock solution and 20 ml of heptane (zero dipole moment) were transferred under argon to a three-necked flask fitted with a reflux condenser and argon gasification means. The reaction mixture was then heated to 100° C./120° C. (internal temperature T° C.), and the catalyst was added. After one hour, during which the reaction was followed by GC after 5, 10, 20, 30 and 60 minutes, the reaction mixture was cooled down to room temperature and the separated carbonate phase was extracted three times with heptane. The combined heptane phases were evaporated, and the yellow-brown residue was analyzed by GC.

Used catalysts: 1 ml of 1M sulphuric acid ($H_2SO_4$), 1 ml of 1 M phosphoric acid ($H_3PO_4$), 19 mg of p-toluenesulphonic acid (p-TsOH) in 10 ml of heptane, 93 mg of Nafion® NR50, Stock solution: 0.6% TMHQ, 0.3% phytadienes, 0.4% (all-rac)-α-tocopherol, 95.6% PTMHQ. All amounts in GC area %, reaction time 60 minutes.

EXAMPLE 4

Cyclization of Phytltrimnethylhydroguinone to (all-arc)-α-tocopherol with Various Concentrations of p-toluenesulphonic Acid A mixture 10 ml of the stock solution and 10 ml of heptane (zero dipole moment) was heated to 100° C. (internal temperature, reflux of heptane) under an argon atmosphere. After 10 minutes at 100° C. the catalyst p-toluenesulphonic acid (p-TsOH), dissolved in propylene carbonate (dipole moment 16.5 D, was added in a syringe. Conversion and selectivity of the reaction were checked by GC after 10, 20, 40, 60 and 180 minutes following completed addition of the catalyst. After three hours 100 ml of heptane were added and the heptane phase was separated. The carbonate phase was extracted three times with 20 ml of heptane and the combined heptane phases were concentrated under vacuum. The resulting brown residue was analyzed by GC. The results of the GC analysis are presented in the following table:

TABLE 4

Various catalyst concentrations

| Time in minutes | 16 mol % p-TsOH | | 8 mol % p-TsOH | | 4 mol % p-TsOH | | 2 mol % p-TsOH | |
|---|---|---|---|---|---|---|---|---|
| | α-Tocopherol | Phytyltrimethyl-hydroquinone | α-Tocopherol | Phytyltrimethyl-hydroquinone | α-Tocopherol | Phytyltrimethyl-hydroquinone | α-Tocopherol | Phytyltrimethyl-hydroquinone |
| 10 | 89.5 | 1.8 | 85.2 | 3.4 | 83.8 | 6.5 | 51.8 | 33.3 |
| 20 | 90.1 | 2.6 | 85.6 | 1.3 | 90.7 | 1.8 | 73.7 | 11.5 |
| 40 | 89.5 | 1.1 | 88.9 | 0.5 | 93.5 | 0.4 | 79.6 | 8.9 |
| 60 | 87.3 | 0.6 | 88.4 | 0 | 94.7 | 0.1 | 90.6 | 1.9 |
| 180 | 85.2 | 0 | 87.7 | 0 | 95.8 | 0 | 93.9 | 0.1 |

66 mg of phosphotungstic acid (HPA), or 0.1 ml of a solution of 50 mg of bis(trifluoromethanesulphonyl)amine (TFMS) in 7.66 ml of propylene carbonate.

The results are presented in the following table:

TABLE 3

Catalyst screening

| Catalyst | Phytadienes (%) | PTMHQ (%) | (all-rac)-α-Tocopherol (%) | T (° C.) |
|---|---|---|---|---|
| $H_2SO_4$ | 0.4 | — | 98.1 | 100 |
| $H_2SO_4$ | 0.7 | — | 95.3 | 120 |
| $H_3PO_4$ | 0.5 | 60.4 | 26.0 | 100 |
| $H_3PO_4$ | 0.8 | 74.1 | 18.1 | 120 |
| p-TsOH | 0.6 | 41.0 | 48.6 | 100 |
| p-TsOH | — | 6.5 | 88.3 | 120 |
| Nafion ® NR50 | 0.6 | 64.8 | 29.2 | 100 |
| Nafion ® NR50 | — | 0.6 | 96.7 | 120 |
| HPA | 0.9 | — | 97.5 | 100 |
| HPA | 0.7 | — | 97.1 | 120 |
| TFMS | 0.8 | 3.6 | 92.4 | 100 |
| TFMS | 0.5 | — | 95.4 | 120 |

EXAMPLE 5

Cyclization of Phytyltrimethylhydroquinone to (all-rac)-α-tocopherol with Various Solvents—Determination of the Reaction Half Times The phytyltrimethylhydroquinone (0.82 g, 1.9 mmol) was transferred under argon to a four-necked flask equipped with inter alia a reflux condenser and argon gasification means, and dissolved in 20 ml of the investigated solvent [heptane (zero dipole moment), γ-butyrolactone (dipole moment 13.7 D), heptane/propylene carbonate (dipole moment 16.5 D) solvent system in the volume ratio 1:1]. The reaction mixture was heated to 120° C. (bath temperature) and 1 mol % of the catalyst p-toluenesulphonic acid (p-TsOH) (1.9 ml of 0.1 mmol in 10 ml of methylene chloride) was added with a syringe. Samples of the reaction mixture were taken after 10, 20, 30, 40, 60 and 120 minutes to check the conversion. From the obtained analytical data reaction half times for each solvent were calculated and correlated with the dipole moment of the investigated solvents. For heptane the reaction was zero order. This situation is appropriate in cases of small conversion. For γ-butyrolactone and heptane/propylene carbonate propylene a first order reaction was observed. After logarithmic calculation of the y-axis the 50% value was taken.

TABLE 5

Solvent effects on the conversion of phytyltrimethylhydroquinone

| Propylene carbonate/Heptane | | | γ-Butyrolactone | | | Heptane | | |
|---|---|---|---|---|---|---|---|---|
| Time in min. | α-Tocopherol | Phytyltrimethyl-hydroquinone | Time in min. | α-Tocopherol | Phytyltrimethyl-hydroquinone | Time in min. | α-Tocopherol | Phytyltrimethyl-hydroquinone |
| 8 | 3.7 | 88.8 | 6 | 3.1 | 88.8 | 10 | 1.3 | 91.9 |
| 18 | 5.9 | 84.2 | 16 | 5.4 | 85.8 | 20 | 1.4 | 90.9 |
| 28 | 9 | 80.1 | 26 | 8.8 | 82.2 | 30 | 1.6 | 89.3 |
| 38 | 11.6 | 77.3 | 36 | 11.8 | 77.6 | 40 | 1.7 | 87.6 |
| 52 | 25.3 | 70.8 | 52 | 18.6 | 62.1 | 60 | 2.2 | 89.6 |
| 120 | 39.3 | 46.1 | 114 | 29.8 | 58.2 | 120 | 4.3 | 84.2 |
| 1101 | 84.46 | 2.4 | 1099 | 70.2 | 13.4 | 1103 | 25.3 | 47.7 |

The invention claimed is:

1. A process for the manufacture of (all-rac)-α-tocopherol, comprising submitting isolated, purified phytyltrimethylhydroquinone to acid catalysis, thereby promoting ring closure to (all-rac)-α-tocopherol.

2. A process according to claim 1, wherein the isolated, purified phytyltrimethylhydroquinone is pure to the extent of at least 95%.

3. A process according to claim 1, wherein the isolated, purified phytyltrimethylhydroquinone is submitted to the acid catalysis in the absence of a solvent.

4. A process according to claim 1, wherein the isolated, purified phytyltrimethylhydroquinone is submitted to the acid catalysis in a solvent or a solvent mixture.

5. A process according to claim 4, wherein the solvent or at least one solvent component of the solvent mixture is one with a dipole moment greater than $9 \times 10^{-30}$ C-m (or 2.7D).

6. A process according to claim 1, wherein the acid catalyst is a Brönsted acid or mixture of two or more Brönsted acids in the absence of any further types of acid catalysts.

7. A process according to claim 1, wherein the isolated, purified phytyltrimethylhydroquinone is submitted to the acid catalysis in the optional presence of a solvent or a solvent mixture, and wherein the amount of (any) solvent used, expressed in terms of the weight percent (wt. %) of the starting material phytyltrimethylhydroquinone relative to the weight of solvent, is such that the wt. % of phytyltrimethylhydroquinone is from about 0.1 to about 100 wt. %.

8. A process according to claim 1, wherein the amount of catalyst relative to the amount of phytyltrimethylhydroquinone employed is from about 0.001 to about 20 wt. %.

9. A process according to claim 1, wherein after completion of the acid catalysis promoting ring closure to (all-rac)-α-tocopherol the reaction mixture is directly treated, with or without removal of the catalyst, with an acetylation agent selected from the group consisting of acetic anhydride, acetic acid and an acetic ester to convert the free tocopherol to (all-rac)-α-tocopherol acetate.

10. A process according to claim 1, wherein the isolated, purified phytyltrimethylhydroquinone is about at least 98% pure.

11. A process according to claim 1, wherein the acid catalysis is effected at temperatures from about 0° C. to about 150° C.

12. A process according to claim 11, wherein the acid catalysis is effected at temperatures from about 90° C. to about 130° C.

13. A process according to claim 7, wherein the amount of the solvent used, expressed in terms of the weight percent (wt. %) of the starting material phytyltrimethylhydroquinone relative to the weight of solvent, is such that the wt. % of phytyltrimethylhydroquinone is from about 2 to about 20 wt.

14. A process according to claim 1, wherein the amount of catalyst relative to the amount of phytyltrimethylhydroquinone employed is from about 0.1 to about 10 wt. %.

15. The process according to claim 1, further comprising prior to acid catalysis of purified phytyltrimethylhydroquinone (PTMHQ), alkylating trimethylhydroquinone (TMHQ) with isophytol (IP) to produce PTMHQ, and isolating and purifying the PTMHQ.

16. The process according to claim 15, wherein the isolated PTMHQ is purified to the extent of at least 95%.

17. The process according to claim 15, wherein the alkylation of TMHQ with IP is carried out with a catalytic amount of trifluoroacetic acid or its anhydride and at least one solvent.

18. The process according to claim 17, wherein the at least one solvent is selected from the group consisting of toluene, heptane, methylene chloride, acetic acid, diethyl ether, benzene, and xylene.

19. The process according to claim 17, wherein the at least one solvent is a two-phase solvent system of ethylene carbonate or propylene carbonate and heptane.

20. The process according to claim 19, wherein the two-phase solvent system is in a volume ratio of from about 0.8:1 to about 1.25:1.

21. The process according to claim 15, wherein the alkylation is carried out at a temperature of from about 20° C. to about 140° C.

22. The process according to claim 21, wherein the alkylation is carried out at a temperature of from about 40° C. to about 120° C.

23. The process according to claim 22, wherein the alkylation is carried out at a temperature of from about 80° C. to about 100° C.

24. A process for the manufacture of (all-rac)-α-tocopherol, comprising alkylating trimethylhydroquinone (TMHQ) with isophytol (IP) to produce phytyltrimethylhydroquinone (PTMHQ), isolating and purifying the PTMHQ, and submitting the isolated, purified PTMHQ to acid catalysis, thereby promoting ring closure to (all-rac)-α-tocopherol.

25. The process according to claim 24, wherein the isolated PTMHQ is purified to the extent of at least 95%.

26. The process according to claim 24, wherein the alkylation of TMHQ with IP is carried out with a catalytic amount of trifluoroacetic acid or its anhydride and at least one solvent.

27. The process according to claim 26, wherein the at least one solvent is selected from the group consisting of toluene, heptane, methylene chloride, acetic acid, diethyl ether, benzene, and xylene.

28. The process according to claim 26, wherein the at least one solvent is a two-phase solvent system of ethylene carbonate or propylene carbonate and heptane.

29. The process according to claim 28, wherein the two-phase solvent system is in a volume ratio of from about 0.8:1 to about 1.25:1.

30. The process according to claim 24, wherein the alkylation is carried out at a temperature of from about 20° C. to about 140° C.

31. The process according to claim 30, wherein the alkylation is carried out at a temperature of from about 40° C. to about 120° C.

32. The process according to claim 31, wherein the alkylation is carried out at a temperature of from about 80° C. to about 100° C.

33. The process according to claim 24, wherein the isolated, purified PTMHQ is submitted to the acid catalysis in the absence of a solvent.

34. The process according to claim 24, wherein the isolated, purified PTMHQ is submitted to the acid catalysis in a solvent or a solvent mixture.

35. The process according to claim 34, wherein the solvent or at least one solvent component of the solvent mixture is one with a dipole moment greater than $9 \times 10^{-30}$ C-m (or 2.7D).

36. The process according to claim 24, wherein the acid catalyst is a Brönsted acid or mixture of two or more Brönsted acids in the absence of any further types of acid catalysts.

37. The process according to claim 24, wherein the isolated, purified PTMHQ is submitted to the acid catalysis in the optional presence of a solvent or a solvent mixture, and wherein the amount of (any) solvent used, expressed in terms of the weight percent (wt. %) of the starting material PTMHQ relative to the weight of solvent, is such that the wt. % of PTMHQ is from about 0.1 to about 100 wt. %.

38. The process according to claim 24, wherein the amount of catalyst relative to the amount of PTMHQ employed is from about 0.001 to about 20 wt. %.

39. The process according to claim 24, wherein after completion of the acid catalysis promoting ring closure to (all-rac)-α-tocopherol the reaction mixture is directly treated, with or without removal of the catalyst, with an acetylation agent selected from the group consisting of acetic anhydride, acetic acid and an acetic ester to convert the free tocopherol to (all-rac)-α-tocopherol acetate.

40. The process according to claim 25, wherein the isolated, purified PTMHQ is about at least 98% pure.

41. The process according to claim 24, wherein the acid catalysis is effected at temperatures from about 0° C. to about 150° C.

42. The process according to claim 41, wherein the acid catalysis is effected at temperatures from about 90° C. to about 130° C.

43. The process according to claim 37, wherein the amount of the solvent used, expressed in terms of the weight percent (wt. %) of the starting material PTMHQ relative to the weight of solvent, is such that the wt. % of PTMHQ is from about 2 to about 20 wt. %.

44. The process according to claim 24, wherein the amount of catalyst relative to the amount of PTMHQ employed is from about 0.1 to about 10 wt. %.

\* \* \* \* \*

UNITED STATES PATENT AND TRADEMARK OFFICE
CERTIFICATE OF CORRECTION

PATENT NO. : 7,626,046 B2  Page 1 of 1
APPLICATION NO. : 10/494005
DATED : December 1, 2009
INVENTOR(S) : Bonrath et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 278 days.

Signed and Sealed this

Second Day of November, 2010

David J. Kappos
*Director of the United States Patent and Trademark Office*